United States Patent
Schaefer

(10) Patent No.: US 9,562,529 B2
(45) Date of Patent: Feb. 7, 2017

(54) TUBE ROLLER PUMP WITH AUTO-ORIENTABLE AND AUTO-LOCKABLE ROTOR AND MEDICAL DEVICE FOR EXTRACORPOREAL BLOOD TREATMENT WITH TUBE ROLLER PUMP

(71) Applicant: B. Braun Avitum AG, Melsungen (DE)

(72) Inventor: Oliver Schaefer, Neuenstein (DE)

(73) Assignee: B. Braun Avitum AG, Melsungen (DE)

( * ) Notice: Subject to any disclaimer, the term of this patent is extended or adjusted under 35 U.S.C. 154(b) by 653 days.

(21) Appl. No.: 13/933,532

(22) Filed: Jul. 2, 2013

(65) Prior Publication Data

US 2014/0012201 A1 Jan. 9, 2014

(30) Foreign Application Priority Data

Jul. 3, 2012 (DE) .................. 10 2012 105 913

(51) Int. Cl.
*F04B 43/12* (2006.01)
*F04B 45/06* (2006.01)
(Continued)

(52) U.S. Cl.
CPC ............... *F04B 43/12* (2013.01); *F04B 43/08* (2013.01); *F04B 43/1253* (2013.01);
(Continued)

(58) Field of Classification Search
CPC ..... F04B 43/12; F04B 43/123; F04B 43/1238; F04B 43/1276; F04B 45/06; F04B 45/065; F04B 45/08; F04B 43/1253; F04B 43/08; F04B 43/09; F04B 43/1223; F04C 15/0073; A61M 1/30; F04D 29/20; F04D 29/29263; F04D 29/266
(Continued)

(56) References Cited

U.S. PATENT DOCUMENTS 3,737,257 A * 6/1973 DeVries .............. F04B 43/1253
417/477.8
4,558,996 A 12/1985 Becker
(Continued)

FOREIGN PATENT DOCUMENTS

DE 85 00 320 5/1985
DE 42 20 119 12/1993
(Continued)

OTHER PUBLICATIONS

European Search Report for EP 13174617.4 dated Oct. 24, 2013.

*Primary Examiner* — Bryan Lettman
*Assistant Examiner* — Timothy Solak
(74) *Attorney, Agent, or Firm* — RatnerPrestia

(57) ABSTRACT

Tube roller pumps for blood treatment devices are disclosed. The pumps include a curved surface with a rotor rotatable therein. The rotor attaches via a shaft reception to a drive shaft of the pump. The rotor has a first locking element for axially locking the rotor on the shaft and a second locking element for rotationally coupling the shaft and the rotor. The shaft reception and the drive shaft guide the rotor to a position on the shaft, when pushed onto the shaft, and, at this position, the first element may be moved by the shaft from locked to released. The rotor, when pushed further onto the shaft, is moved to another position at which the first element is automatically moved back to locked and the second element may be brought into manual engagement with the shaft to transmit torque from the shaft to the rotor.

15 Claims, 10 Drawing Sheets

(51) Int. Cl.
*F04B 43/08* (2006.01)
*F04D 29/20* (2006.01)
*F04D 29/26* (2006.01)
*A61M 1/30* (2006.01)

(52) U.S. Cl.
CPC .............. *F04B 45/06* (2013.01); *F04D 29/20* (2013.01); *A61M 1/30* (2013.01); *F04D 29/266* (2013.01)

(58) Field of Classification Search
USPC ....................................................... 417/476
See application file for complete search history.

(56) References Cited

U.S. PATENT DOCUMENTS

| | | | |
|---|---|---|---|
| 5,062,775 A | | 11/1991 | Orth |
| 5,681,257 A | * | 10/1997 | Letourneur ............... B04B 9/08 403/325 |
| 6,095,772 A | * | 8/2000 | Ramey ................. F04D 29/044 417/319 |
| 7,547,200 B2 | | 6/2009 | O'Mahony et al. |
| 2010/0129247 A1 | | 5/2010 | Lauer |
| 2010/0166578 A1 | * | 7/2010 | Watson ................... F04D 13/10 417/423.3 |

FOREIGN PATENT DOCUMENTS

| | | | | |
|---|---|---|---|---|
| DE | 10 2007 020 573 | | 11/2008 | |
| WO | WO 2007/038364 | | 4/2007 | |
| WO | WO 2007/080499 | * | 7/2007 | .............. F04B 43/12 |

\* cited by examiner

TUBE ROLLER PUMP WITH AUTO-ORIENTABLE AND AUTO-LOCKABLE ROTOR AND MEDICAL DEVICE FOR EXTRACORPOREAL BLOOD TREATMENT WITH TUBE ROLLER PUMP

CROSS REFERENCE TO RELATED APPLICATIONS

This application claims priority to German Patent Application No. DE 10 2012 105 913.6 filed Jul. 3, 2012, the contents of such application being incorporated by reference herein.

FIELD OF THE INVENTION

The present invention relates to a tube roller pump (peristaltic pump) for a medical device for extracorporeal blood treatment, comprising a pump housing including a curved running surface (bearing surface) and a rotor that is rotatable within the running surface, a tube segment being adapted to be placed between the running surface and the rotor. The rotor is adapted to be attached via a shaft reception means to a drive shaft of the tube roller pump, and at least one locking element is provided for axially locking and/or rotationally coupling the rotor to the drive shaft.

The invention additionally relates to a medical device for extracorporeal blood treatment, which comprises such a tube roller pump.

BACKGROUND INFORMATION

In medical devices for extracorporeal blood treatment (dialysis) tube roller pumps are frequently used, which convey the blood drawn from the patient to a dialyzer and return it to the patient. Such tube roller pumps operate peristaltically, with a loop-shaped tube segment abutting on an appropriately curved running surface of the pump housing. A pump rotor, which is located within the running surface, then moves with its outer edges, or rather with rollers attached thereto, along the tube segment. In so doing, it locally squeezes the tube thus allowing, on the basis of the elastic properties of the material of the tube segment, blood to be conveyed through the tube segment. To this end, the blood is supplied to the tube segment via a first connection and removed therefrom via a further connection at the other end of the tube segment. The tube segment thus forms, e.g. together with the supply and discharge lines and a plurality of air traps, a so-called transfer system with which the patient's blood is conveyed to a dialyzer and back to the patient.

DESCRIPTION OF THE RELATED ART

German patent application DE 10 2007 020 573 A1, by way of example, discloses such a tube roller pump with a stator, a rotor and a rotor drive, in the case of which a tube is placed between the rotor and the tube roller path of the stator. By rotation of the rotor and the resultant revolving movement of tube rollers, the tube is pressed against the tube roller path of the stator so that liquid is pumped through the tube.

Also U.S. Pat. No. 7,547,200 B2 discloses such a peristaltic pump with a rotor and rollers, which press an inserted tube against a semicircular tube roller track. The roller track has at one end thereof a beveled edge for receiving the tube, which is attached to a cartridge.

SUMMARY OF THE INVENTION

The transfer systems used for such pumps in the field of medical technology are normally exchanged after each treatment and not reused for other patients. Therefore, a used tube segment must be removed from the pump prior to installing a new transfer system in the device.

In addition, also the rotor of such a system is normally removed after each treatment for the purpose of cleaning, and reinstalled after cleaning. In order to simplify the handling of the rotor during this operation, systems have already been developed which make use of radial and axial positive locking for transmitting torque from the drive shaft to the rotor. Rotors having this kind of structural design may especially be provided with bayonet locking devices in combination with an additional locking element. The additional locking element may e.g. be a lever that must be turned for locking the rotor. However, such systems necessitate at least four handling steps during the installation operation, since the second locking element must first be turned for rotational coupling, before the rotor can be attached to the drive shaft and rotated by approx. 90° so as to lock the bayonet locking device. Subsequently, the locking element must be turned again to finally lock the rotor.

It is therefore an object of the present invention to provide a tube roller pump for a medical device for extracorporeal blood treatment, which comprises a rotor and allows said rotor to be installed with the least possible number of easily executable handling steps.

It is also an object of the present invention to provide a medical device for extracorporeal blood treatment, which includes a tube roller pump suitable for having installed therein such a rotor.

According to aspects of the invention, this object is achieved by a tube roller pump (peristaltic pump) according to the independent claim 1. Advantageous further developments of the tube roller pump can be seen from subclaims 2-12. An object is also achieved by a medical device for extracorporeal blood treatment according to claim 13.

The tube roller pump according to aspects of the present invention, which is used for a medical device for extracorporeal blood treatment, comprises a pump housing including a curved running surface (bearing surface) and a rotor that is rotatable within the running surface, a tube segment being adapted to be placed between the running surface and the rotor. The rotor is adapted to be attached via a shaft reception means to a drive shaft of the tube roller pump, and at least one locking element is provided for axially locking and/or rotationally coupling the rotor to the drive shaft.

According to aspects of the invention, the rotor has provided thereon a first locking element for selective axial locking of the rotor on the drive shaft and a second locking element for selective rotational coupling of drive shaft and rotor. The geometry of the shaft reception means of the rotor and that of the drive shaft are configured such that the rotor is adapted to be guided to a first predetermined rotary position relative to the drive shaft, when it is axially pushed onto the drive shaft. At this first position, the first locking element is adapted to be moved by the drive shaft from a locking position to a release position. The rotor, when pushed further onto the drive shaft, is thus adapted to be moved to a second, axially defined position at which the first locking element is adapted to be moved back to the locking position, in particular automatically, and the second locking element is adapted to be brought, in particular manually, into engagement with the drive shaft such that a torque can be transmitted from the drive shaft to the rotor.

Due to this structural design of the rotor and of the drive shaft of the pump, the rotor is, on the one hand, auto-orientable, since it will automatically be guided to the correct, radially defined position, when the operator pushes the rotor axially onto the drive shaft. At this position, the rotor can be radially locked by the second locking element, so that a torque can be transmitted from the drive shaft to the rotor. The rotor is here automatically rotated to the correct position by the user, and the geometry supports the user in finding this position. This makes the installation process much easier for the operator.

On the other hand, the rotor is also auto-lockable, since it is automatically locked by the first locking element during the attachment process, without any extra activity being necessary on the part of the operator during the process of installation. Prior to installation, the locking element already occupies the locking position from which it is only temporarily moved to the release position by the drive shaft before it is automatically returned. Hence, the temporary unlocking does not necessitate any additional activity either, but the drive shaft unlocks the locking element automatically during the installation process, and the first locking element is configured such that it will automatically be relocked, when the rotor has arrived at a second, axially defined position. At this position, the rotor also occupies an axially defined position in which the second locking element can be brought into engagement with the drive shaft so as to prevent relative rotation between the rotor and the drive shaft or establish a rotational coupling therebetween.

Hence, the rotor is ready for use at this position, and the first locking element can axially lock the rotor preferably only at this position. The previously radially defined position allows axial locking of the rotor and the positioning of the drive shaft relative to the second locking or force transmitting element.

Taking all this into account, it is therefore possible to establish, with only one handling step, axial locking and anti-rotation locking of a releasable shaft-to-collar connection. In particular, the system allows single hand operation, since the rotor can be grasped with one hand by the user, and pushed onto the drive shaft. In the demounted condition of the rotor, it is also easily possible to clean the drive shaft.

One embodiment of the invention is so conceived that, at the first, radially defined position, the first locking element is adapted to be moved by means of the drive shaft from a locking position to a release position against the force of a spring, whereas, at the second, axially defined position, it is adapted to be moved back to the locking position by the force of said spring. Automatic unlocking and renewed locking, caused by the axial movement of the rotor on the drive shaft, can thus be realized easily.

The drive shaft and the shaft reception means may both have slide geometries sliding along one another, whereby the rotor, while being axially pushed onto the drive shaft, is guided to the first, radially defined position relative to the drive shaft. A preferred embodiment is so conceived that, at the first, radially defined position, the first locking element is then adapted to be moved from the locking position to the release position through the slide geometry of the drive shaft. This has the advantage that the slide geometry of the drive shaft can be used for rotationally orientating the rotor relative to the drive shaft as well as for unlocking the first locking element.

The slide geometry of the drive shaft may e.g. be defined by a gable-shaped end portion, whereby two oblique surfaces are formed. These oblique surfaces then slide along the complementary slide geometry of the shaft reception means, whereby the rotor will rotate to the desired rotary position. Furthermore, the oblique surfaces push the first locking element to the side, which has the effect that also the locking element slides along an oblique surface.

According to one embodiment of the invention, the slide geometry of the shaft reception means is defined by two triangular plates, which are formed on the inner wall of the shaft reception means and extend in parallel opposed relationship with one another, a tip of each of these triangular plates pointing in the direction of the rotor bottom. The gable-shaped end portion of the drive shaft can thus slide along the triangular plates, and the rotor is rotated to a defined, radial position in this way. Preferably, the drive shaft then has, below the gable-shaped end portion, two opposed parallel side faces and the parallel surfaces of the triangular plates in the interior of the shaft reception means abut on the parallel side faces of the drive shaft at the first, radially defined position of the rotor.

The second locking element preferably includes a groove and is adapted to be manually moved to a position at which opposed inner surfaces of this groove abut on the side faces of the drive shaft. To this end, the second locking element is e.g. adapted to be pivoted about a pivot shaft within a reception means in the rotor. At a first open position of the radial locking element, the groove will then not act on the side faces of the drive shaft, but when the locking element is turned in the direction of the drive shaft, the groove will engage the drive shaft from above and then abut on the side faces of the drive shaft.

The first locking element may have different structural designs and may be adapted to the geometry of the drive shaft in different ways, so that the latter can be axially locked. The locking element may e.g. engage a locking geometry in the drive shaft, when occupying the locking position. According to one embodiment of the invention, the first locking element is a metal sheet or safety metal sheet, which extends transversely to the drive shaft and engages a radial groove of the drive shaft, when occupying the locking position. The groove is preferably configured as a radial, circumferentially extending groove, so that the rotor, after having reached the second, axially defined position, can still be rotated about the drive shaft, when the second locking element is not locked. For locking the second locking element, it would only be necessary to manually return the rotor to a radial position, at which a positive locking engagement can be established between the groove of the radial locking element and the flat side faces of the drive shaft.

The first locking element may, however, also have a different structural design and comprise e.g. one or a plurality of pins. Also friction-based locking elements may be used, provided that they comprise components that can be contacted and moved when the rotor is pushed onto the drive shaft. It would, however, also be possible to use systems in which the movement of the rotor on the drive shaft causes automatic unlocking and locking in some other way. Magnetic or electronic systems would here be imaginable.

In order to be able to manually release the axial locking of the rotor, prior to pulling the rotor off the drive shaft e.g. after a therapy, the rotor may additionally include an operating element by means of which the first locking element can be moved manually from the locking position to the release position. According to one embodiment of the invention, the manual operating element is a lever that can be turned manually so as to release the locking. Also a push-button switch may be used, alternatively or additionally, as a manual operating element.

The invention additionally comprises a medical device for extracorporeal blood treatment, comprising a tube roller pump including a pump housing having a curved running surface and a rotor that is rotatable within the running surface, a tube segment of an extracorporeal blood circuit being adapted to be placed between the running surface and the rotor. The tube roller pump is here configured according to an embodiment of the tube roller pump according to aspects of the present invention.

BRIEF DESCRIPTION OF THE DRAWINGS

The invention is best understood from the following detailed description when read in connection with the accompanying drawings. Included in the drawings are the following figures:

FIG. 3b shows a schematic top view of a rotor according to FIG. 3a;

FIG. 4b shows a schematic top view of a rotor according to FIG. 4a;

FIG. 5b shows a schematic top view of a rotor according to FIG. 5a;

FIG. 6b shows a schematic top view of a rotor according to FIG. 6a.

DETAILED DESCRIPTION OF THE PREFERRED EMBODIMENTS

Figure 1:
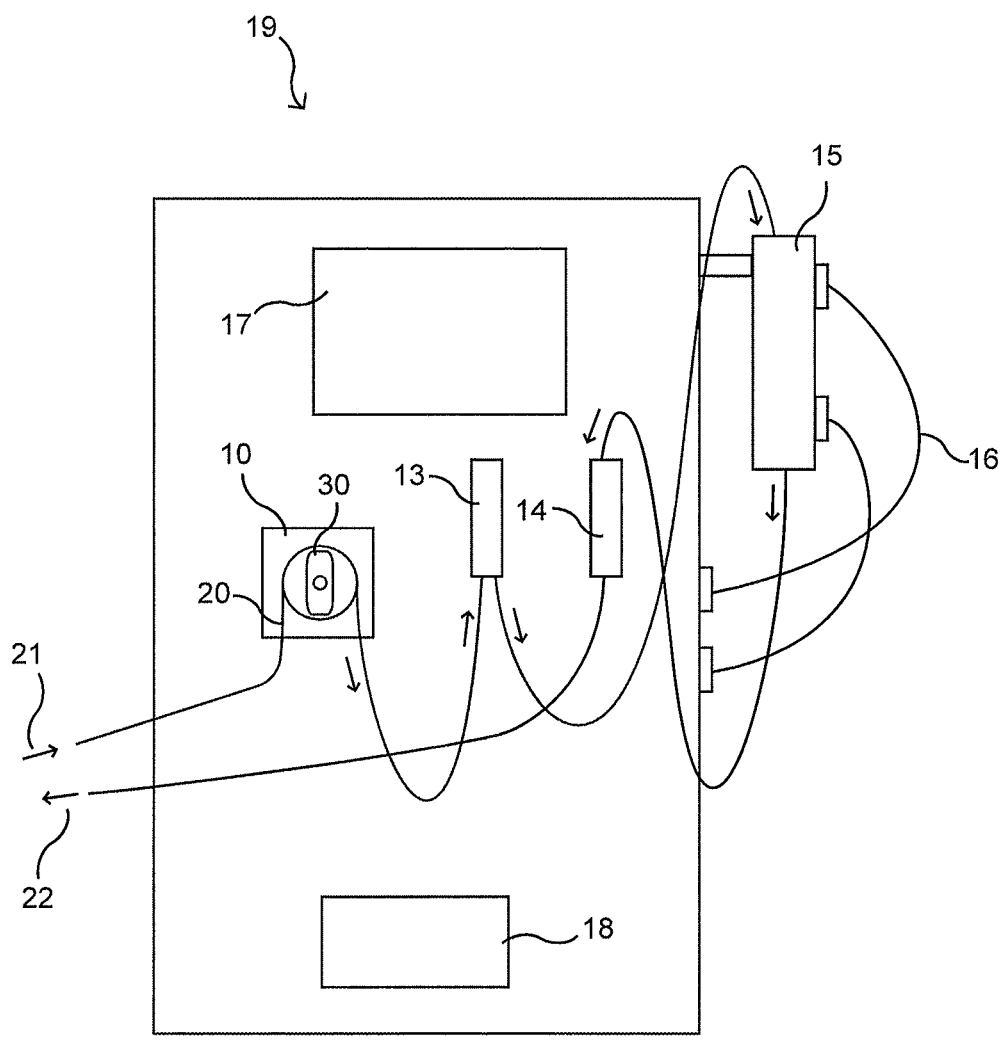
FIG. 1 shows a schematic representation of a medical device for extracorporeal blood treatment with a blood pump.

FIG. 1 shows a schematic representation of the essential basic components of a medical device 19 for extracorporeal blood treatment including a blood pump, the blood pump being a tube roller pump, or a peristaltic pump. The tube roller pump includes a pump housing 10, which is typically arranged on the front of the dialysis machine 19.

This tube roller pump has supplied thereto arterial blood 21 of a patient, which is then conveyed through the extracorporeal blood circuit. Subsequently, the blood is returned to the patient as venous blood 22. In so doing, the blood is conveyed by means of the pump through a transfer system connected to a plurality of components of the dialysis machine, a tube segment 20 of the transfer system being inserted in the blood pump and a rotor 30 conveying the blood peristaltically through this tube segment 20, as can be seen from an enlarged view according to FIG. 2.

After having passed through the blood pump, the blood arrives at the dialyzer 15 after having preferably passed through an arterial air trap 13. In the dialyzer 15 the blood is purified through an exchange of substances with a dialysate 16, which is supplied to and discharged from the dialyzer 15. After having passed through the dialyzer 15, the blood arrives at a venous air trap 14 and is then returned to the patient. This circuit of the patient's blood is identified by arrows in FIG. 1.

The setting of dialysis parameters and therapy monitoring can be executed via a display/input unit 17, which is preferably configured as a touch screen. Furthermore, the dialysis machine 19 includes a control unit 18.

Figure 2:
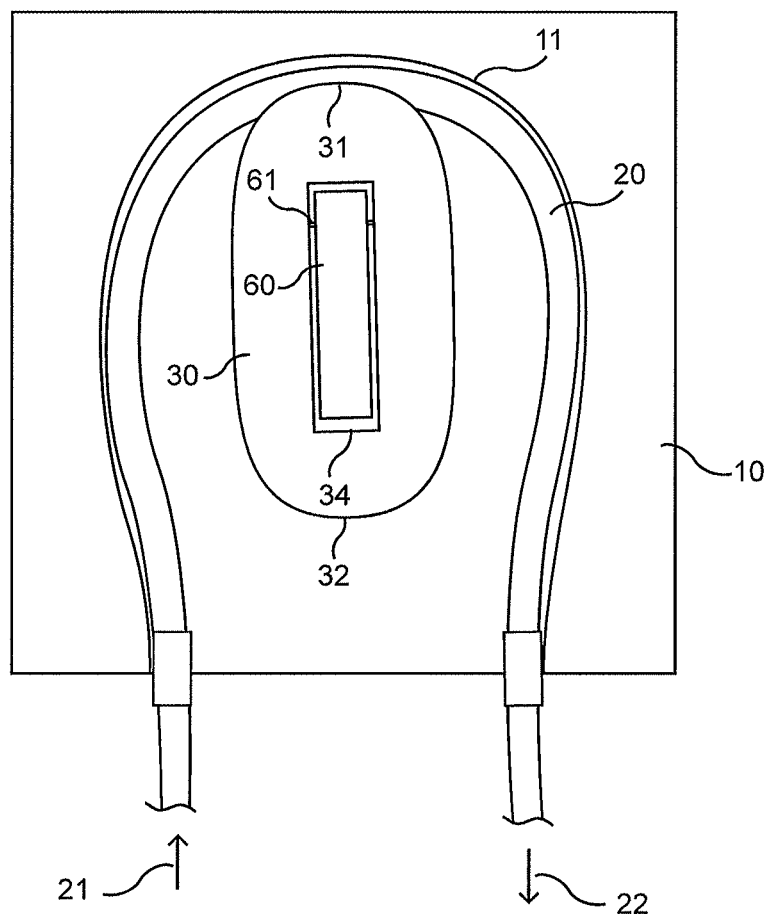
FIG. 2 shows a schematic top view of a tube roller pump having a tube segment and a rotor inserted therein.

FIG. 2 shows a schematic representation of a top view of a tube roller pump having the tube segment 20 and the rotor 30 inserted therein. The tube roller pump is easily accessible for the operator of the machine, and the pump housing 10 is adapted to be covered by a lid, which is not shown and which is adapted to be pivoted e.g. upwards or to the side via a hinge so as to gain access to the tube segment 20.

The pump housing 10 has formed therein a curved running surface (bearing surface) 11, which is defined by a recess in the housing and into which the tube segment 20 can be inserted in a loop shape such that the two tube ends project beyond the housing 10 at the bottom. The recess may be formed in the pump housing 10 with a lateral surface, which extends perpendicular to the front of the machine in a substantially uniform manner, or the running surface 11 is formed in a non-uniform manner by a lateral surface of the recess, which is concave in shape or even twisted in itself.

The running surface 11 has arranged therein a rotor 30 having e.g. an approximately elliptical circumference so that, when rotating, it will be able to slightly compress the tube segment 20 at the main crowns 31, 32 by means of rollers, which are not shown. The clockwise rotation of the rotor 30 has the effect that also the area of a compressed tube segment moves clockwise until the associated main crown 31, or rather the roller attached thereto, detaches itself from the tube segment. Meanwhile, the opposite main crown 32 has, however, moved into contact with the tube segment 20 once more, so that blood is conveyed peristaltically from the pump inlet to the pump outlet in the respective tube segment area ahead of the area in which the tube compressed by the rotor 30.

Figure 3A:
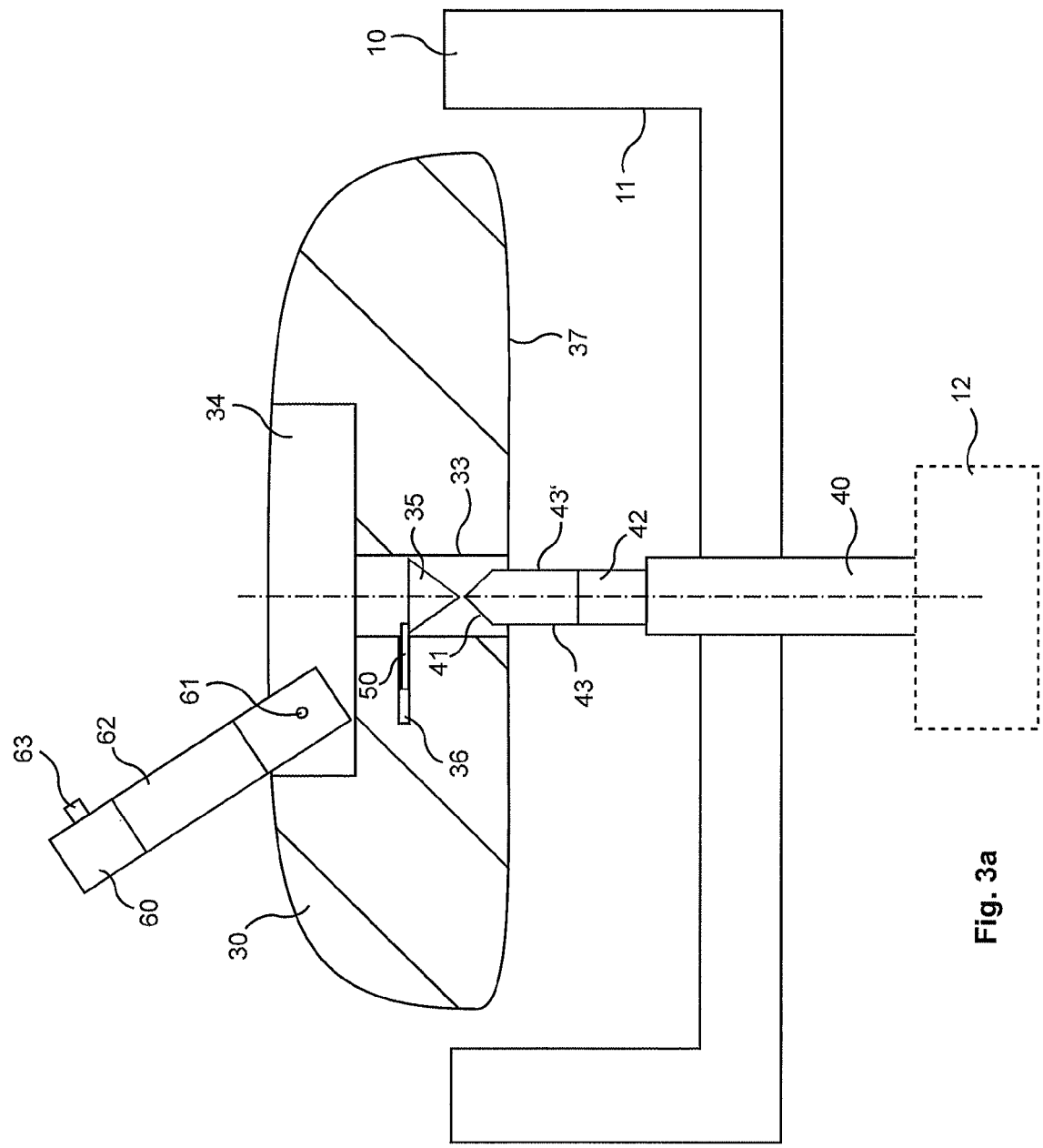
FIG. 3a shows a schematic side view of a rotor at the beginning of the operation of pushing the rotor onto the drive shaft of a tube roller pump.

FIG. 3a shows a schematic representation of a rotor 30 at the beginning of mounting the rotor on a drive shaft 40 of a tube roller pump. The drive shaft 40 is located within the pump housing 10 in which the running surface 11 for accommodating the tube segment is formed. The drive shaft 40 of the pump is simultaneously the output shaft or transmission output shaft of a drive 12, which is only indicated by a broken line in FIG. 3a.

In the middle of the rotor 30 a shaft reception means 33 is provided, so that the rotor 30 can be pushed onto the drive shaft 40. The shaft reception means 33 is substantially hollow-cylindrical in shape, but has a different geometry in certain areas thereof, e.g. triangular plate surfaces 35, 35' on the inner surface of the shaft reception means 33. For transmitting the torque from the drive shaft 40 to the rotor 30, a (second) locking element or anti-rotation element or force transmitting element 60 is provided in the upper area of the rotor 30, i.e. on the rotor side facing away from the drive 12. This anti-rotation element 60 is supported within a reception means 34 in the rotor 30 such that it is pivotable about a shaft 61 so that it can be pivoted between a release and a locking position. The anti-rotation element 60 additionally includes a groove 62, an end portion of the drive shaft 40 being in positive locking engagement with this groove 62 at the locking position. In addition, the anti-rotation element 60 may have provided thereon a crank handle 63 for manual emergency operation. In the situation shown in FIG. 3a, i.e. prior to the mounting of the rotor 30 on the drive shaft, the anti-rotation element 60 is pivoted to the left, i.e. outwards, and unlocked. However, the radial anti-rotation element 60 need not be open so as to allow the rotor 30 to be installed in the therapy or operating position, since, due to the geometries of the drive shaft 40 and the shaft reception means 33, the rotor 30 is automatically guided to a specific relative rotary position, at which the upper end of the drive shaft 40 is in positive locking engagement with the groove 62 of the anti-rotation element 60.

In the area of the shaft reception means 33, a (first) locking element 50 for axially fixing the rotor 30 on the drive shaft 40 is additionally arranged, said locking element 50 projecting radially inwards into the shaft reception means 33 in the locking position. This locking element 50 is mounted in a radially movable manner within a recess 36 in the rotor 30, and is preferably spring-loaded and biased radially inwards by the force of a spring (which is not shown) and forced towards the shaft reception means 33. In the interior of the drive shaft 40 e.g. a circumferentially extending groove 42 is provided, the locking element 50 engaging said groove 42 at the locking position so that the rotor 30 is axially locked in position on the drive shaft 40. Locking may, however, also be accomplished by any other geometries of the drive shaft 40, which are adapted to be brought into locking engagement with the locking element 50.

For inserting the rotor 30 into the pump, it can be grasped by an operator and pushed onto the drive shaft 40, the anti-rotation element 60 being unlocked or pivoted out of the way in this condition. The geometries of the drive shaft 40 and of the shaft reception means 33 are configured and adapted to one another such that the rotor 30 is automatically guided to a first, defined rotary position relative to the drive shaft 40. To this end, the end portion 41 of the drive shaft 40 facing the rotor 30 is wedge-shaped so that two oblique wedge surfaces are formed, which slope to the left and to the right in FIG. 3a. These oblique surfaces merge with two opposed, planar side faces or flat portions 43 and 43' on the drive shaft 40, which extend parallel to the axis of rotation of the drive shaft 40.

Additionally, two triangular plates 35 and 35', tube inner surfaces extend parallel to the axis of rotation of the rotor 30, are formed within the shaft reception means 33 on the inner wall thereof. In the representation according to FIG. 3a only the rear plate 35 is shown. A second triangular plate 35' extends parallel to the first plate 35 on the opposite side of the shaft reception means 33, which is cut off in the view according to FIG. 3a. The plates 35 and 35' define an isosceles triangle and are oriented such that the tip of the respective triangle points in the direction of the rotor bottom 37.

Figure 3B:
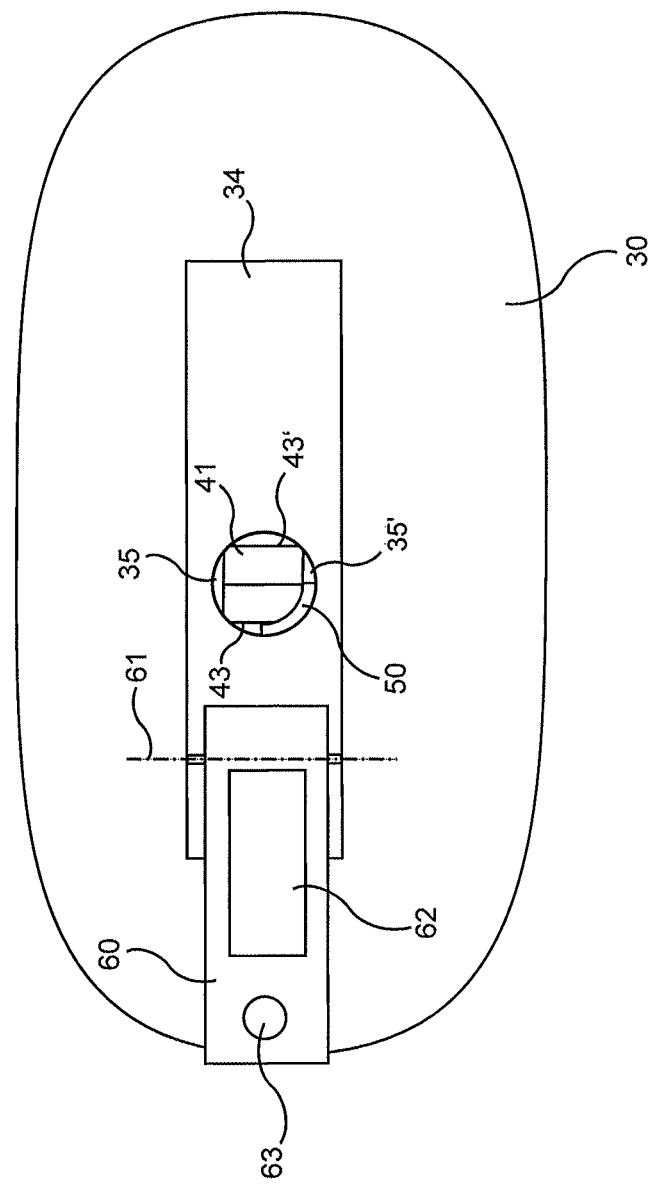

In the situation shown in FIG. 3a, the rotor 30 has been positioned by a user on the drive shaft 40 such that the tip of the wedge shaped end portion of the drive shaft 40 approximately meets the two tips of the triangular plates 35 and 35'. This can also be seen from the top view according to FIG. 3b, which shows the two opposed triangular plates 35 and 35' within the shaft reception means 33. The locking element 50 is (still) located above the plates 35, 35', and the upper edge of the wedge-shaped front of the drive shaft 40 is oriented transversely to the inner surfaces of the plates 35, 35'. Furthermore, this view shows the planar side faces 43 and 43' of the drive shaft 40, which are also oriented transversely to the plates 35, 35'.

Since in this position the outer sections of the wedge-shaped end portion 41 of the drive shaft 40 meet the tip of plate 35 and plate 35', respectively, the rotor 30 cannot be attached to the drive shaft 40. In response to slight rotation and pressure, the wedge surfaces of the wedge-shaped end portion 41 of the drive shaft 40 will, however, slide along the flanks or sides of the triangular plates 35, 35', thus forcing the rotor 30 into a rotation, which will be discerned by the user, who can then follow this rotation with his hand. When, starting from the orientation shown in FIG. 3a and FIG. 3b, the rotor 30 and the drive shaft 40 have been rotated relative to one another by 90°, they occupy the rotary position or orientation shown in FIGS. 4a and 4b, where the planar side faces 43 and 43' of the drive shaft 40 now point to the front. Hence, they are oriented such that they extend parallel to the inner surfaces of the triangular plates 35 and 35' (in FIG. 4a behind the drive shaft). Furthermore, the wedge surfaces of the end portion 41 of the drive shaft 40 now slope to the front and to the back.

Figure 4A:
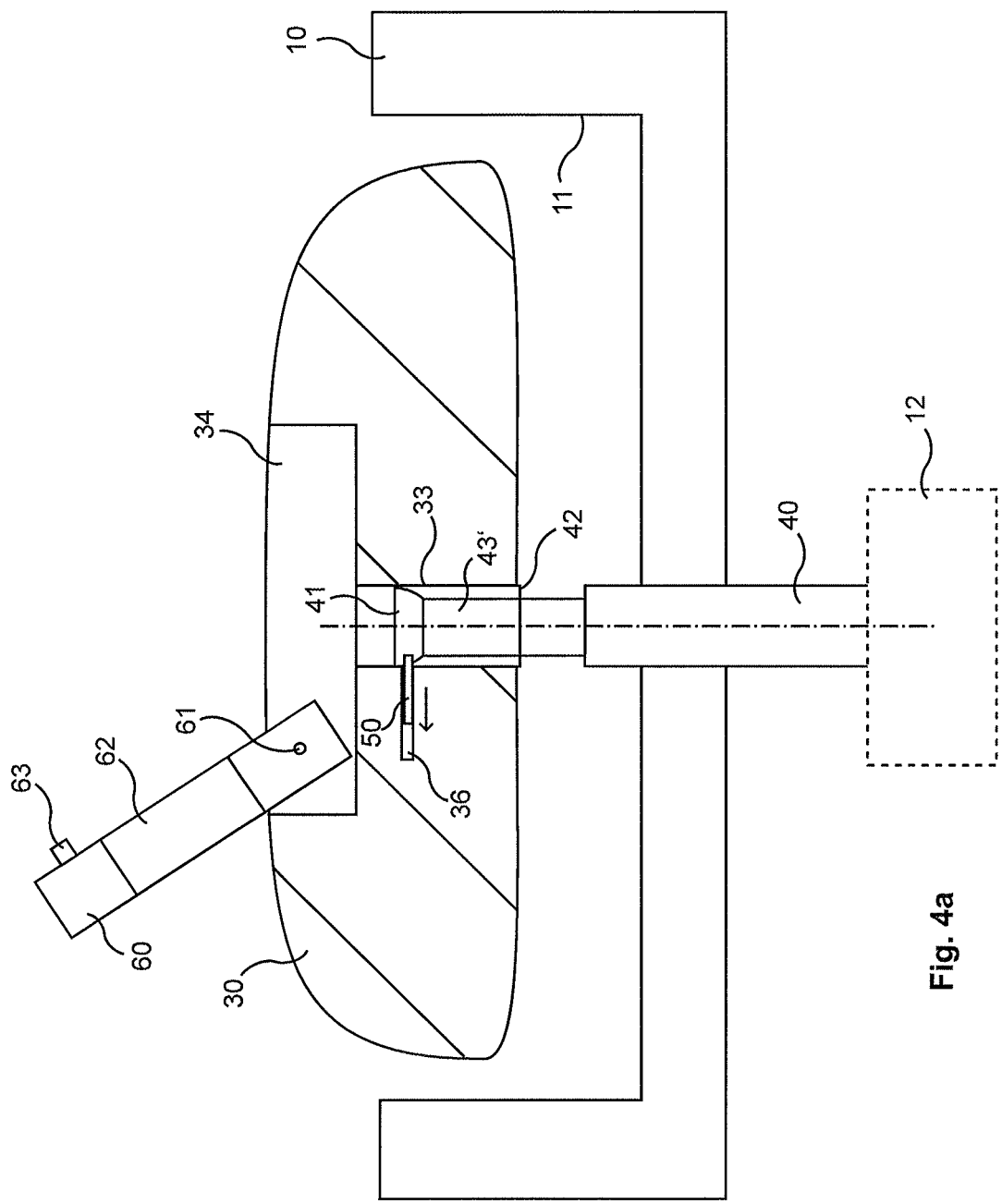
FIG. 4a shows a schematic side view of a rotor according to FIG. 3a during unlocking of a first locking element.
Figure 4B:
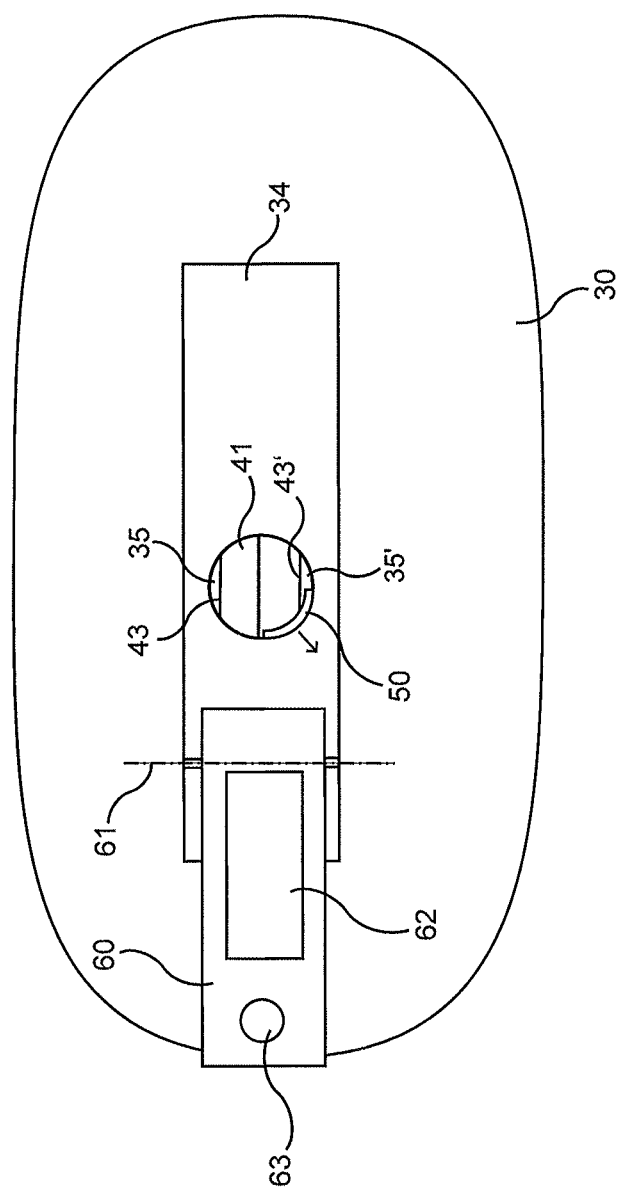
Figure 5A:
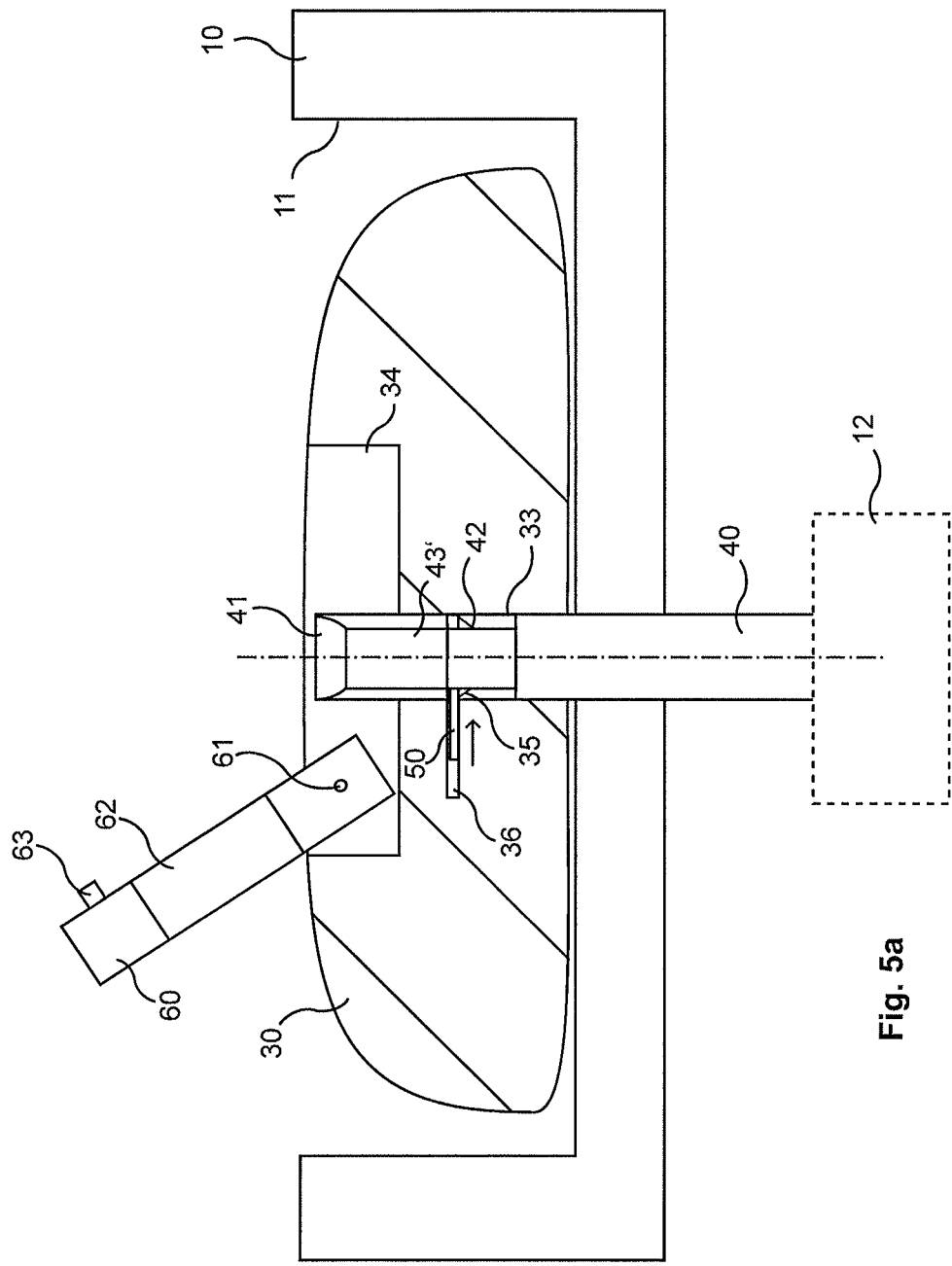
FIG. 5a shows a schematic side view of a rotor according to FIG. 3a during locking of the first locking element.

This can also be seen from the top view according to FIG. 4b, where the side faces 43 and 43' now abut on the inner surfaces of the plates 35 and 35'. The plates 35, 35' and consequently also the side faces 43, 43' of the drive shaft 40 are here preferably oriented parallel to the longitudinal axis of the rotor 30. At the position shown in FIGS. 4a and 4b, the rotor 30 and the drive shaft 40 occupy a first, defined rotary position relative to one another, but the rotor 30 is, in principle, prevented from being pushed further onto the drive shaft 40 because it is blocked by the locking element 50. However, the rotor 30 and the oblique wedge surfaces in the end portion of the drive shaft 40 now have a defined orientation, in which the locking element 50 contacts one of the wedge surfaces such that the wedge surface is able to radially displace the locking element 50 outwards into the recess 36 against a spring force of the radially inwards biased locking element 50, when the rotor 30 is advanced in the radial direction. This movement of the locking element 50 is illustrated in FIGS. 4a and 4b by an arrow pointing to the left and to the lower left, respectively. In the course of this movement, the locking element 50 slides along the wedge-shaped end portion 41 of the drive shaft 40, whereby the rotor 30 can be pushed further onto the drive shaft 40 until it finally arrives at a second, axially defined position, which is shown in FIG. 5a. Attention should in this respect, be paid to the fact that the recess 36, in which the locking element 50 is radially guided, as can especially be seen in FIG. 4a, should be arranged in the defined, first relative rotary position of the drive shaft 40 such that it is located laterally of the edge of the wedge-shaped end portion 41, that the locking element 50 should only come into contact with one of the wedge surfaces, but not with the wedge edge, and that it should be possible to guarantee that the locking element 50 can slide along the wedge surfaces. This can be accomplished in that, as shown in FIG. 4a, the recess 36 and the locking element 50 are located more on the side of one of the triangular plates 35, 35' defining the orientation of the drive shaft 40 and consequently of the wedge surfaces. Furthermore, also the inward radial movement of the locking element 50 should be limited, e.g. by a stop (not shown), so as to prevent the locking element 50 from moving to a position in which it overlaps the wedge edge.

Figure 5B:
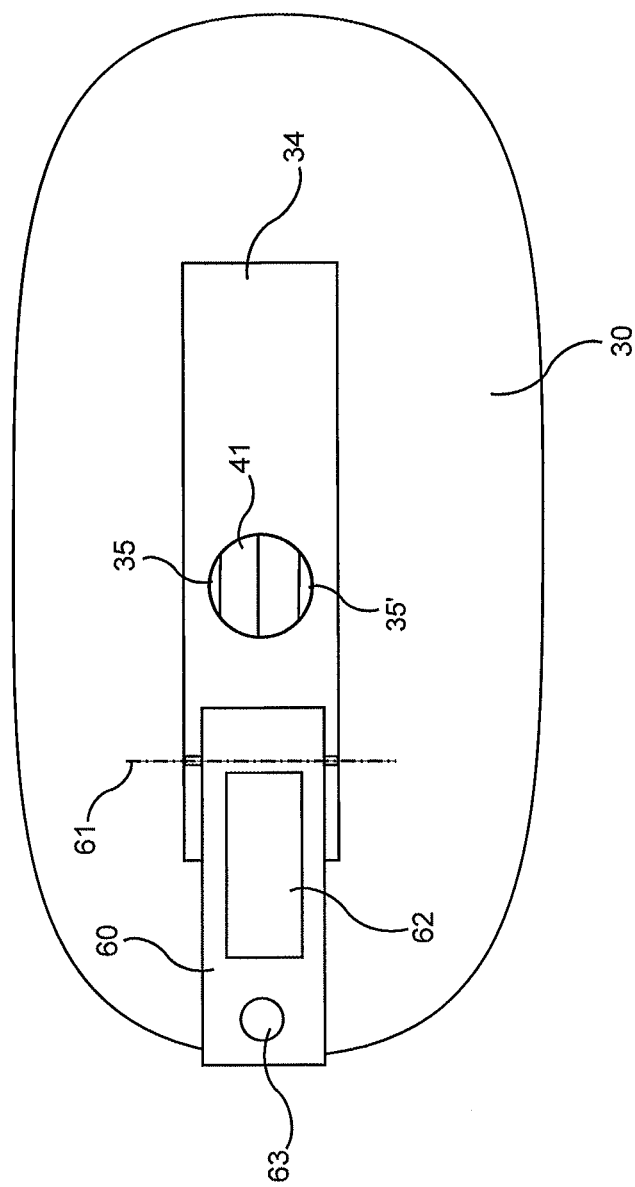

At the axially defined position shown in FIG. 5a, the groove 42 of the drive shaft 40 is located in the area of the locking element 50, so that the latter, acted upon by the force of the spring, will move into, and consequently engage the groove 42. This movement of the locking element 50 is illustrated in FIG. 5a by an arrow pointing to the right. The locking element 50 then abuts inside, i.e. from below on a side wall of the groove 42 and is no longer visible in the top view of FIG. 5b. The width of the groove 42 and the axial height of the triangular plates 35 and 35' are chosen such that the tips of the plates 35 and 35' come, at this position, into contact with the other (lower) side wall of the groove 42, so that the rotor 30 can, on the one hand, no longer be pulled off the drive shaft and, on the other hand, no longer be pushed further onto the drive shaft 40. The rotor 30 is thus secured against axial movements on the drive shaft 40. Alternatively, the width of the groove 42 and the thickness of the locking element 50 can be adapted to one another such that the locking element 50, in cooperation with the groove 42, alone prevents an axial relative movement of the rotor 30 and of the drive shaft 40.

When the groove is a groove 42 that extends circumferentially in the radial direction, the rotor 30 can no longer be pulled off the drive shaft 40, but it can be rotated on the drive shaft 40 until the radial anti-rotation element 60 is operated. This means that, at the position at which the anti-rotation element 60 is pivoted out of the way, i.e. to the side, axial locking is given, but the rotor 30 may be rotated making use of the crank handle 63, e.g. for manual emergency operation. The patient's blood can thus be returned manually from the line system to the patient in an emergency operation, without any risk of the rotor 30 slipping off the drive shaft 40 while the crank handle is being operated.

Figure 6A:
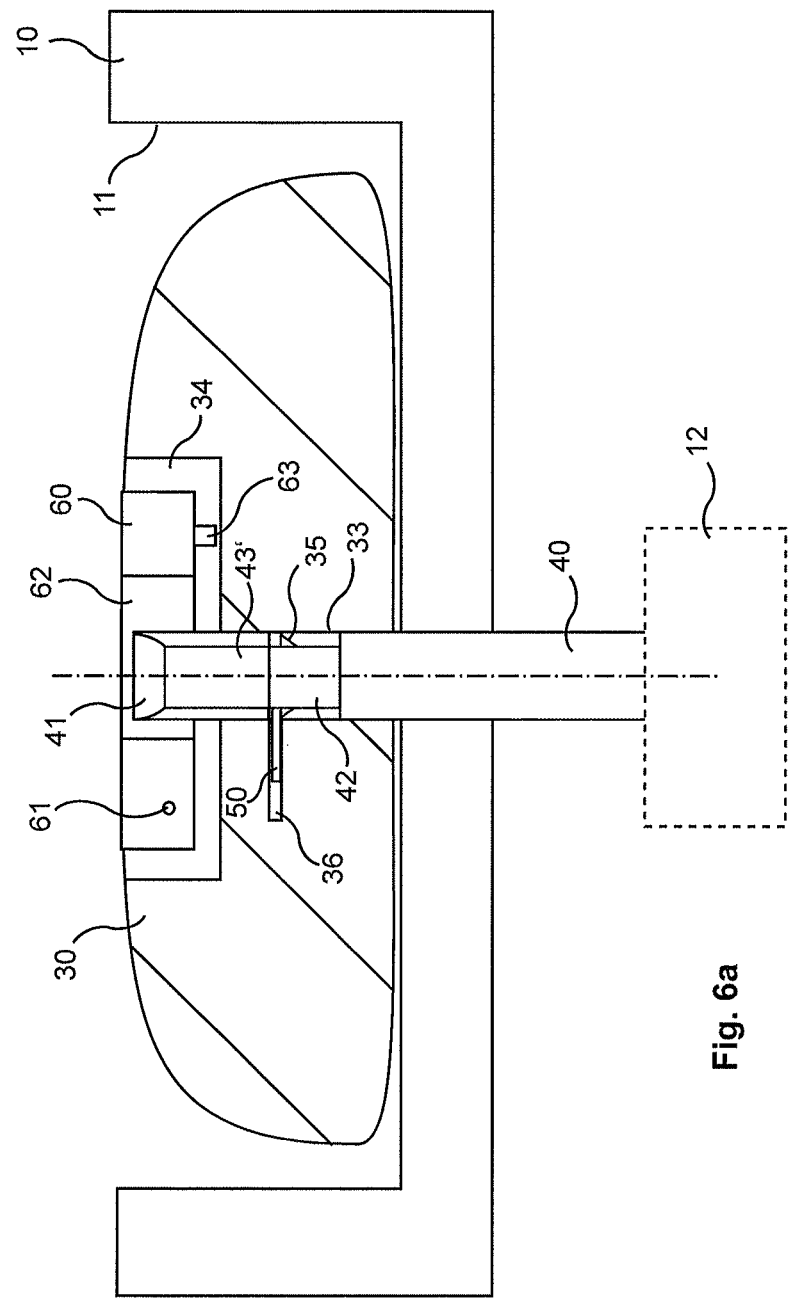
FIG. 6a shows a schematic side view of a rotor according to FIG. 3a with a locked second locking element.
Figure 6B:
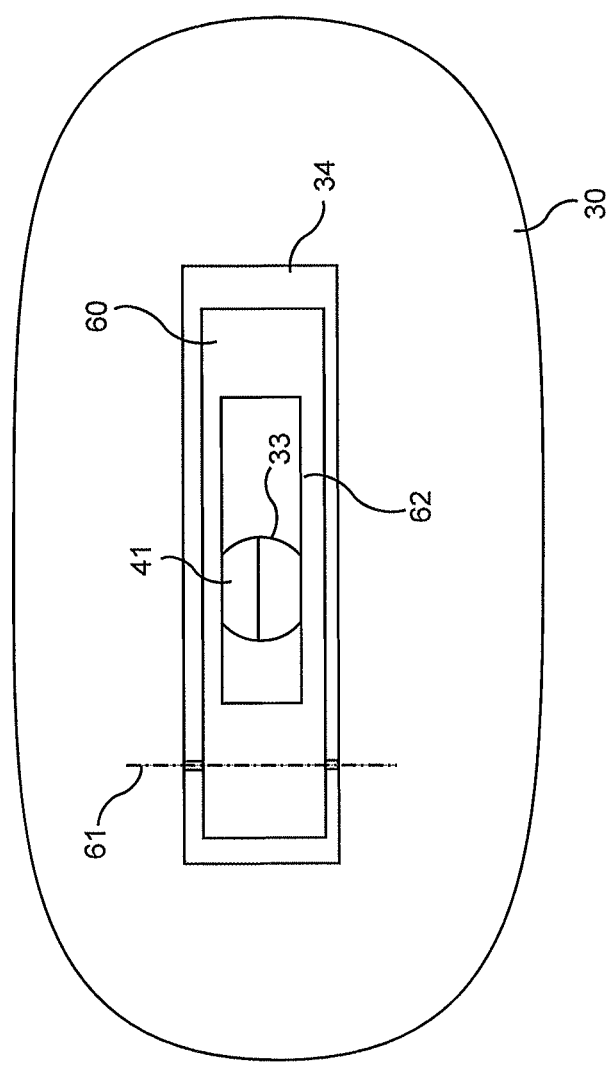

In order to accomplish also radial locking of the rotor 30 for a therapy, i.e. for the operating position of the rotor, the anti-rotation element 60 is pivoted about the shaft 61, which extends perpendicular to and in spaced relationship with the axis of rotation of the rotor, onto the drive shaft 40, as shown in the situation according to FIG. 6a. The inner surfaces of the groove 62 within the anti-rotation element 60 will then abut on the side faces 43 and 43' of the drive shaft 40 in large area contact therewith, so that, due to the positive locking engagement, a relative rotation between the drive shaft 40 and the rotor 30 will no longer be possible and a torque can be transmitted from the drive shaft 40 to the rotor 30. From FIG. 6a it can additionally be seen that the crank handle 63 may simultaneously serve as a stop so as to limit the pivotal movement of the anti-rotation element 60 at the locking position.

For demounting the rotor 30 after a therapy, the anti-rotation element 60 may again be pivoted away (in FIG. 6a to the left) and thus be unlocked. This is, however, not absolutely necessary, but the anti-rotation means may also be released by simply pulling the rotor 30 off the drive shaft 40. To this end, the axial locking element 50 must be released so that the rotor 30 can be pulled off the drive shaft 40. The rotor 30 may have provided thereon a manual operating element for this purpose. This operating element may e.g. be a lever, which is turned for moving the locking element 50 against the force of the spring from the locking position radially outwards to the release position. After the removal of the rotor 30, this lever may be turned once more, so that, before the rotor 30 is reattached to the drive shaft 40, the locking element 50 will again occupy the locking position so as to allow the above described connection to be realized by executing only one handling step. The lever may, however, also be so conceived that, due to the force of the spring, it will automatically return to the position in which the locking element 50 occupies the locking position, as has already been described hereinbefore.

However, the manual operating element may also be e.g. a push-button switch on the rotor 30, which has to be pressed by an operator for pulling off the rotor 30. Preferably, the switch is positioned such that it can be pressed while grasping the rotor 30. When the switch is pressed, the locking element 50 is caused to move to the release position, but the locking element 50 will return automatically to the locking position, when the push-button switch is released. This can again be accomplished by the force of a spring. Alternatively, an additional push-button switch may be provided so as to cause the locking element 50 to move from the release position to the locking position.

Furthermore, the radial anti-rotation element 60 may also have a structural design other than that of a pivotable component. It may, for example, be an insert, e.g. a slide, with a handle element, which is adapted to be moved to and fro within the recess 34 in the rotor 30 by the user. In this case, the insert has formed therein a groove, which, when the insert is correctly oriented with respect to the rotor and consequently the drive shaft, establishes the positive locking engagement with the drive shaft 40, when the insert is forced into the rotor 30 or pushed onto the rotor 30. For the purpose of unlocking, the insert has to be slightly pulled out or away from the rotor 30.

In comparison with this embodiment of an anti-rotation element, the above described variant is, however, advantageous insofar as a crank handle 63 for manual emergency operation can be integrated more easily in the anti-rotation element 60, since in the case of a pivotable anti-rotation element 60 the crank handle 63 is moved away from the axis of rotation of the rotor 30 in the direction of the edge of the rotor 30.

The invention claimed is:

1. A tube roller pump for a medical device for extracorporeal blood treatment, comprising:
  a pump housing including a curved running surface and a rotor that is rotatable within the running surface, wherein
  a tube segment is adapted to be placed between the running surface and the rotor, and the rotor is adapted to be attached via a shaft reception means to a drive shaft of the tube roller pump, and wherein
  at least one locking element is provided for axially locking and/or rotationally coupling the rotor to the drive shaft, wherein the rotor has provided thereon:
    a first locking element for selective axial locking of the rotor on the drive shaft and
    a second locking element for selective rotational coupling of the drive shaft and the rotor, wherein
  a geometry of the shaft reception means is configured such that the rotor is adapted to be guided to a first predetermined rotary position relative to the drive shaft, when it is axially pushed onto the drive shaft, and that, at this first predetermined rotary position, the first locking element is adapted to be moved by the drive shaft from a locking position to a release position, whereby the rotor, when pushed further onto the drive shaft, is adapted to be moved to a second, axially defined position at which the first locking element is adapted to be moved back to the locking position, and the second locking element is adapted to be brought into engagement with the drive shaft such that a torque is transmitted from the drive shaft to the rotor;
  wherein the drive shaft and the shaft reception means both have slide geometries sliding along one another, when the rotor, while being axially pushed onto the drive shaft, is guided to the first position relative to the drive shaft; and
  wherein the slide geometry of the shaft reception means is defined by two triangular plates, which are formed on an inner wall of the shaft reception means and have inner surfaces that extend parallel to an axis of rotation of the rotor and are arranged in an opposed relationship with one another, and wherein a tip of each of these triangular plates points in the direction of a bottom of the rotor.

2. The tube roller pump according to claim 1, wherein, at the first predetermined rotary position, the first locking element is adapted to be moved by means of the drive shaft from the locking position to the release position against a force of a spring, whereas, at the second position, the first locking element is adapted to be moved back to the locking position by the force of said spring.

3. The tube roller pump according to claim 1, wherein, at the first predetermined rotary position, the first locking element is adapted to be moved from the locking position to the release position through contact with the slide geometry of the drive shaft.

4. The tube roller pump according to claim 1, wherein the slide geometry on the drive shaft is defined by a wedge-shaped end portion, whereby two wedge surfaces inclined at an angle relative to the axis of rotation of the drive shaft are formed.

5. The tube roller pump according to claim 1, wherein, at the first predetermined rotary position of the rotor, the inner surfaces of the triangular plates in an interior of the shaft reception means abut on coplanar side faces in contact therewith, said side faces being formed on two opposed sides of the drive shaft.

6. The tube roller pump according to claim 5, wherein the second locking element includes a groove and is adapted to be manually moved to a position at which opposed inner surfaces of this groove abut on the side faces of the drive shaft in contact therewith.

7. The tube roller pump according to claim 1, wherein the second locking element is adapted to be pivoted about a pivot shaft within the rotor, said pivot shaft extending in a spaced relationship with the axis of rotation of the rotor.

8. The tube roller pump according to claim 7, wherein the pivot shaft extends perpendicular to the axis of rotation of the rotor.

9. The tube roller pump according to claim 1, wherein, when occupying the locking position, the first locking element engages a locking geometry in the drive shaft.

10. The tube roller pump according to claim 1, wherein the first locking element is a flat sheet metal part, which is movable relative to the axis of rotation of the rotor and which, at the locking position, engages a circumferentially extending groove of the drive shaft.

11. The tube roller pump according to claim 1, wherein the rotor includes an operating element, by which the first locking element can be moved manually from the locking position to the release position.

12. The tube roller pump according to claim 11, wherein the operating element is a lever or a push-button switch.

13. A medical device for extracorporeal blood treatment, comprising:
an extracorporeal blood circuit;
a dialyzer configured to purify blood of a patient;
a control unit; and
a tube roller pump including a pump housing having a curved running surface and a rotor that is rotatable within the running surface, a tube segment of an extracorporeal blood circuit being adapted to be placed between the running surface and the rotor, wherein
the tube roller pump is configured according to claim 1.

14. The tube roller pump according to claim 1, wherein the first locking element is adapted to be moved back to the locking position automatically.

15. The tube roller pump according to claim 1, wherein the second locking element is adapted to be brought into engagement with the drive shaft manually.

* * * * *